United States Patent
Timmis et al.

(10) Patent No.: US 7,530,197 B2
(45) Date of Patent: May 12, 2009

(54) AUTOMATED SYSTEM AND METHOD FOR HARVESTING AND MULTI-STAGE SCREENING OF PLANT EMBRYOS

(75) Inventors: Roger Timmis, Olympia, WA (US); Edwin Hirahara, Federal Way, WA (US); Harry G. Folster, Tacoma, WA (US); Heather Surerus-Lopez, Renton, WA (US)

(73) Assignee: Weyerhaeuser Co., Federal Way, WA (US)

( * ) Notice: Subject to any disclaimer, the term of this patent is extended or adjusted under 35 U.S.C. 154(b) by 1025 days.

(21) Appl. No.: 10/853,491

(22) Filed: May 24, 2004

(65) Prior Publication Data

US 2004/0267457 A1    Dec. 30, 2004

Related U.S. Application Data

(60) Provisional application No. 60/509,070, filed on Jun. 30, 2003.

(51) Int. Cl.
| | |
|---|---|
| A01C 1/06 | (2006.01) |
| A01C 21/00 | (2006.01) |
| A01C 1/00 | (2006.01) |
| A01B 79/00 | (2006.01) |
| A01B 79/02 | (2006.01) |
| A01G 1/00 | (2006.01) |
| A01H 3/00 | (2006.01) |

(52) U.S. Cl. .............. 47/57.6; 47/58.1 R; 47/58.1 SE; 47/DIG. 9

(58) Field of Classification Search ................ 47/57.6, 47/58.1, 58.1 R, 58.1 SE, DIG. 9
See application file for complete search history.

(56) References Cited

U.S. PATENT DOCUMENTS 5,284,765 A    2/1994   Bryan et al.

(Continued)

FOREIGN PATENT DOCUMENTS

DE        2 139 567        3/1973

(Continued)

OTHER PUBLICATIONS

Ibaraki Y et al., "Automation of somatic embryo production," *Plant Cell, Tissue and Organ Cult*, 65:179-199 (2001).

(Continued)

*Primary Examiner*—Kent Bell
(74) *Attorney, Agent, or Firm*—Christensen O'Connor Johnson Kindness

(57) ABSTRACT

A method and system for automatically harvesting and screening plant embryos in multiple stages to identify those embryos that are suited for incorporation into manufactured seeds are provided. The method includes generally three steps. First, plant embryos are automatically sorted according to their rough size/shape and also singulated into discrete embryo units, for example by vibrational sieving. Second, the sorted and singulated plant embryos are classified using a first classification method. For example, each embryo may be imaged by a camera and the image is used to ascertain the embryo's more precise size/shape. Third, for those embryos that have passed the first classification method, a second classification method is applied. For example, a pre-developed classification algorithm to classify embryos according to their putative germination vigor may be applied to the same image used in the first classification method, to identify those embryos that are likely to germinate.

25 Claims, 4 Drawing Sheets

U.S. PATENT DOCUMENTS

| | | | |
|---|---|---|---|
| 5,917,927 | A | 6/1999 | Satake et al. |
| 5,956,413 | A | 9/1999 | Oste et al. |
| 6,117,678 | A | 9/2000 | Carpetner et al. |
| 6,150,167 | A | 11/2000 | Carpenter et al. |
| 6,354,770 | B1 | 3/2002 | McKinnis |
| 6,684,564 | B1 * | 2/2004 | Hirahara .................... 47/57.6 |

FOREIGN PATENT DOCUMENTS

| | | |
|---|---|---|
| GB | 1 507 365 | 4/1978 |
| WO | WO 91/00781 | 1/1991 |
| WO | WO 95/05064 | 2/1995 |
| WO | WO 99/63057 | 12/1999 |
| WO | WO 01/13702 | 3/2001 |

OTHER PUBLICATIONS

Gupta PK, et al., "Development of an Embryogenic System for Automated Propagation of Forest Trees," Cell Cult & Som Cell Gen of Plants 8:75-93, 1991.

Hamalainen JJ et al., "Classification of Plant Somatic Embryos by Computer Vision," Biotech & Bioeng 41(1):35-42, Jan. 1993.

Harrell RC et al., "Automated, In Vitro Harvest of Somatic Embryos," Plant Cell, Tiss & Organ Cult 39:171-183, 1994.

Ibaraki Y, "Image Analysis for Sorting Somatic Embryos," Somatic Embr in Wood Plants 4:169-188, 1999.

Kurata K et al., "A Thinning-Based Algorithm for Evaluating Somatic Embryos," Amer Soc of Ag Eng 36(5):1486-1489, Sep./Oct. 1993.

Roberts DR et al., "A Delivery System for Naked Somatic Embryos of interior Spruce," Autom & Enviro Control in Plant Tiss Cult, pp. 245-256, 1995.

Warren GS et al., "A Physical Method for the Separation of Various States in the Embryogenesis of Carrot Cell Cultures," Plant Sci Letters 9:71-76, 1977.

Timmis R, "Bioprocessing for Tree Production in the Forest Industry: Conifer Somatic Embryogenesis," *Biotech Prog* 1998 (14) pp. 156-166.

Gupta PK et al., "Somatic Embryo Developmenrt in Liquid Medium for Large-sale Propagation of Conifer Trees," *Challenges of plant and agriculture sciences to the crisis of biosphere on earth in 21 Century*, Watanabe K (ed), p. 303.

Timmis R et al, "Use of Visible and Near Infrared Reflectance Spectra for Selection of Germination-Competent Somatic Embryos," *Tree Biotechnology 2003*, Abstract and Poster, Sweden, Jun. 2003.

* cited by examiner

AUTOMATED SYSTEM AND METHOD FOR HARVESTING AND MULTI-STAGE SCREENING OF PLANT EMBRYOS

CROSS REFERENCE TO RELATED APPLICATION

The present application claims the benefit of U.S. Provisional Application No. 60/509,070, filed Jun. 30, 2003.

FIELD OF THE INVENTION

The invention is directed generally to manufactured seeds and, more particularly, to a method and system for automatically harvesting and screening mass-produced plant embryos in multiple stages to identify those embryos that are suited for incorporation into manufactured seeds.

BACKGROUND OF THE INVENTION

Reproduction of selected plant varieties by tissue culture has been a commercial success for many years. The technique has enabled mass production of genetically identical selected ornamental plants, agricultural plants and forest species. The woody plants in this last group have perhaps posed the greatest challenges. Some success with conifers was achieved in the 1970s using organogenesis techniques wherein a bud, or other organ, was placed on a culture medium where it was ultimately replicated many times. The newly generated buds were placed on a different medium that induced root development. From there, the buds having stems and roots were planted in soil.

While conifer organogenesis was a breakthrough, costs were high due to the large amount of handling needed. There was also some concern about possible genetic modification. It was a decade later before somatic embryogenesis achieved a sufficient success rate so as to become the predominant approach to conifer tissue culture. With somatic embryogenesis, an explant, usually a seed or seed embryo, is placed on an initiation medium where it multiplies into a multitude of genetically identical immature embryos. These can be held in culture for long periods and multiplied to bulk up a particularly desirable clone. Ultimately, the immature embryos are placed on a development medium where they grow into somatic analogs of mature seed embryos. As used in the present description, a "somatic" embryo is a plant embryo developed by the laboratory culturing of totipotent plant cells or by induced cleavage polyembryogeny, as opposed to a zygotic embryo, which is a plant embryo removed from a seed of the corresponding plant. These embryos are then individually selected and placed on a germination medium for further development. Alternatively, the embryos may be used in artificial seeds, known as manufactured seeds.

There is now a large body of general technical literature and a growing body of patent literature on embryogenesis of plants. Examples of procedures for conifer tissue culture are found in U.S. Pat. Nos. 5,036,007 and 5,236,841 to Gupta et al.; U.S. Pat. No. 5,183,757 to Roberts; U.S. Pat. No. 5,464,769 to Attree et al.; and U.S. Pat. No. 5,563,061 to Gupta. Further, some examples of manufactured seeds can be found in U.S. Pat. No. 5,701,699 to Carlson et al., the disclosure of which is hereby expressly incorporated by reference. Briefly, a typical manufactured seed is formed of a seed coat (or a capsule) fabricated from a variety of materials such as cellulosic materials, filled with a synthetic gametophyte (a germination medium), in which an embryo surrounded by a tube-like restraint is received. After the manufactured seed is planted in the soil, the embryo inside the seed coat develops roots and eventually sheds the restraint along with the seed coat during germination.

One of the more labor intensive and subjective steps in the embryogenesis procedure is the selective harvesting from the development medium of individual embryos suitable for germination (e.g., suitable for incorporation into manufactured seeds). The embryos may be present in a number of stages of maturity and development. Those that are most likely to successfully germinate into normal plants are preferentially selected using a number of visually evaluated screening criteria. A skilled technician evaluates the morphological features of each embryo embedded in the development medium, such as the embryo's size, shape (e.g., axial symmetry), cotyledon development, surface texture, color, and others, and manually plucks desirable embryos out of the development medium with a pair of tweezers. The plucked desirable embryos are then carefully laid out on a tray in a two-dimensional array for further processing. This is a highly skilled yet tedious job that is time consuming and expensive. Further, it poses a major production bottleneck when the ultimate desired output will be in the millions of plants.

It has been proposed to use some form of instrumental image analysis for embryo selection to supplement or replace the visual evaluation described above. For example, PCT Application Serial No. PCT/US00/40720 (WO 01/13702 A2) discloses an embryo delivery system for manufactured seeds including an imaging camera, which acquires and digitally stores images of embryos. The images are then sent to a computer, which classifies the embryos according to their desirability (i.e., likelihood to germinate and grow into normal plants) based on predetermined parameters (axial symmetry, cotyledon development, surface texture, color, etc.) using a classification method disclosed in PCT Application Serial No. PCT/US99/12128 (WO 99/63057). Those embryos that are classified as desirable are thereafter removed by mini-robotic pick and place systems and inserted into manufactured seeds. The disclosure of these two PCT applications is hereby expressly incorporated by reference.

While instrumental imaging analysis and subsequent automatic insertion of desirable embryos into manufactured seeds have been successful in increasing the efficiency of the embryogenesis procedure, there has not been a complete automated process of harvesting embryos, e.g., removing embryos from a development medium, sorting embryos according to their size/shape and singulating them into discrete units (e.g., by removing any undesirable tissues or other debris), and classifying them according to their desirability for incorporation into manufactured seeds. In other words, there has not been an automated process that could replace the current manual operation of plucking desirable embryos out of a development medium and placing them in an array suitable for further maturation treatments. The present invention is directed to providing a complete automated process of harvesting somatic embryos, which could replace the current manual operation.

SUMMARY OF THE INVENTION

The present invention provides a method and system for automatically harvesting plant embryos. According to one aspect, the automatic harvesting method of the invention screens plant embryos in multiple stages to identify those embryos that are suited for incorporation into manufactured seeds, i.e., those embryos that are both physically fit for incorporation into manufactured seeds (not too big, not too small, not too bent, etc.) and also qualitatively determined to be likely to germinate and grow into normal plants. The automatic harvesting method includes generally three steps. First, plant embryos are automatically sorted according to their size/shape and also singulated into discrete embryo units. For example, the embryos may be washed off from a development medium (e.g., from a development pad) using aqueous liquid and sieved through a porous material. During sieving, the embryos may be further sprayed with aqueous liquid to facilitate removal and washing away of any undesirable material, such as undersized embryos, tissues, and residual embryonal suspensor masses (ESM), through the holes of the porous material. In one preferred embodiment, the porous material is formed as a moving porous conveyor belt so that the embryos being sorted and singulated are simultaneously transported to the subsequent classification stage. Second, the sorted and singulated plant embryos are classified using a first classification method. For example, each of the embryos may be imaged by a camera and the image is used to ascertain the embryo's size/shape. Those embryos within a predefined size/shape range are considered to have passed the first classification method. Third, at least for those embryos that have passed the first classification method, a second classification method is applied to further select those embryos desirable for incorporation into manufactured seeds. For example, a pre-developed classification algorithm to classify embryos according to their putative germination vigor (i.e., likelihood of successful germination) may be applied to the same image used in the first size/shape classification method, to identify those embryos that are likely to germinate. The embryos that have passed both the first and second classification methods are identified as suitable for incorporation into manufactured seeds.

According to one aspect, the first and second classification methods are carried out along a classification conveyor belt while the sorted and singulated embryos are transported thereon. In some classification methods, it is preferred that the embryos are generally arranged in a single file on the classification conveyor belt. Various means for achieving the single file configuration are proposed. For example, the classification conveyor belt may be arranged generally perpendicularly to the porous conveyor belt on which the embryos are sorted and singulated. According to this configuration, the sorted and singulated embryos transported to the end of the porous conveyors may drop therefrom by gravity onto the classification conveyor belt to generally form a single file thereon. To achieve sufficient spacing between the embryos in a single file, the initial rate of washing off embryos from a development medium onto the porous conveyor belt or the speed of the porous conveyor belt may be adjusted, perhaps based on the actual rate of embryos being dropped from the porous conveyor belt onto the classification conveyor belt as observed by a suitable optical scanning system.

According to another aspect, the method further includes the step of automatically removing those undesirable embryos that have failed the first or second classification method from the classification conveyor belt. For example, a computer-controlled air or liquid jet may be used to eject undesirable embryos. The precise timing of the jet activation can be computer controlled because the position of each undesirable embryo is precisely known based on the firing time of the camera that has imaged each embryo and the speed of the classification conveyor belt.

According to yet another aspect, the method further includes the step of automatically removing those desirable embryos that have passed both the first and second classification methods from the classification conveyor belt. In one embodiment, the desirable embryos are automatically transferred onto a receiving surface in an evenly spaced array, suitable for various further maturation treatments. For example, the receiving surface may be provided by a tray mounted on a motorized platform configured to adjust the position of the tray relative to the classification conveyor belt. By adjusting the position of the tray based on the known position of each desirable embryo as it is dropped from the classification conveyor belt, the desirable embryos may be received on the tray in an evenly spaced two-dimensional array.

According to yet another aspect, the method may include a step of automatically removing those desirable embryos that have passed one or more initial classification methods from a conveyor belt. For example, a mini-robotic system may be used to pick up those embryos determined to be within an acceptable size/shape range and to precisely place them in an evenly spaced two-dimensional array on a receiving tray. At this time, the embryos may be oriented uniformly, for example, with their cotyledon ends facing the same direction. The properly oriented and precisely spaced apart embryos in a tray may then be forwarded to receive further treatments, for example, drying and subsequent further classification methods. Thereafter, these properly oriented and spaced apart embryos in a tray can be readily transferred and inserted into manufactured seeds which, advantageously, may be arranged in a correspondingly evenly spaced array.

Classifying the embryos in multiple stages achieves efficient screening of embryos. For example, by classifying embryos using a relatively less sophisticated and less time-consuming classification method first, one can reduce the number of embryos to be forwarded to the second classification method that is more sophisticated and more time-consuming. Thus, by carefully selecting suitable classification methods to be combined, one can achieve increasingly selective and discriminating classification of embryos in a time efficient manner. Also, the present invention offers a complete automated process of harvesting somatic embryos, including sorting and singulating embryos (starting with removing the embryos from a development medium), classifying the sorted and singulated embryos according to their putative germination vigor, and further arranging those embryos classified as desirable in a manner suitable for further maturation treatments, e.g., in an evenly spaced two-dimensional array on a tray. Thus, an automated harvesting method and system of the present invention could replace the current manual operation of plucking desirable embryos from a development medium.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

The invention pertains to a method and system for automatically harvesting and screening mass-produced embryos, such as somatic embryos, preferably in multiple stages of increasing complexity to identify those embryos that are suited for incorporation into manufactured seeds. As used herein, an embryo suited for incorporation into a manufactured seed means an embryo that is both biochemically matured (i.e., likely to germinate and grow into a normal plant) and morphologically or physically suited for incorporation into a manufactured seed (i.e., having a size/shape appropriate to be included in a manufactured seed).

Figure 1A:
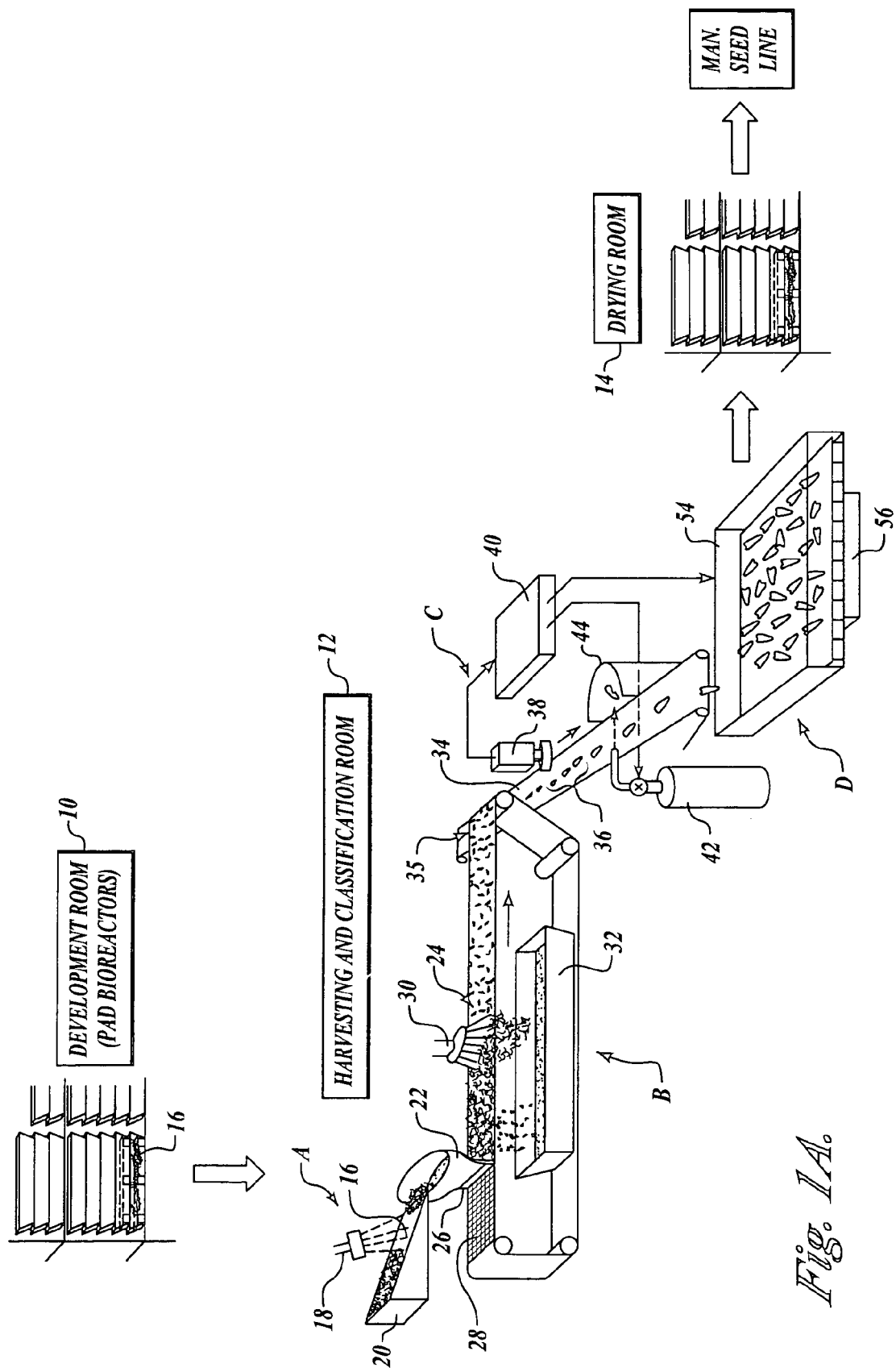
FIG. 1A schematically illustrates a system for automated harvesting and multi-stage screening of plant embryos, in accordance with the present invention.

Referring to FIG. 1A, in a Development Room 10, somatic embryos have been developed from embryonal suspensor masses (ESM) and supported/suspended in or on a development surface 16. A development surface may be provided by a development pad, as illustrated, or may be provided by any other suitable development medium including a gel-form medium, or may further be provided by an intervening surface that is placed on a development medium such as a stainless steel mesh. While the following description illustrates a case in which a development pad is used to provide a development surface, it should be understood that a development surface, as used in the present application, refers to any surface that supports or suspends embryos that are developed from ESM.

Methods of developing somatic embryos are known and described in various publications, as discussed in the background section above. Desirable embryos are to various degrees attached to and embedded in suspensor tissues and residual underdeveloped ESM (or culture material) in the pad 16, together with incompletely developed embryos, abnormally formed embryos, undersized or oversized embryos, and other pieces of non-embryo plant material. The embryos suspended in a development pad 16 are forwarded to a Harvesting and Classification Room 12, in which the embryos (embedded in the culture material) are removed from the development pad and further automatically sorted, singulated, and classified according to their desirability. Classification may be carried out using multiple stages of increasingly sophisticated and yet time-consuming classification methods, to achieve progressively higher selection accuracy and operational efficiency. Those embryos that are classified as desirable are thereafter forwarded to receive further maturation treatments, for example, to a Post Development Treatment Room (Drying Room in the illustrated embodiment) 14 to be dried for storage and subsequent incorporation into manufactured seeds. The present invention is generally directed to the automated process of harvesting and classifying embryos, which occurs in the Harvesting and Classification Room 12. It is contemplated that the harvesting and classification are carried out preferably in a humid clean room conditioned to sustain viability of the embryos being processed.

Figure 2:
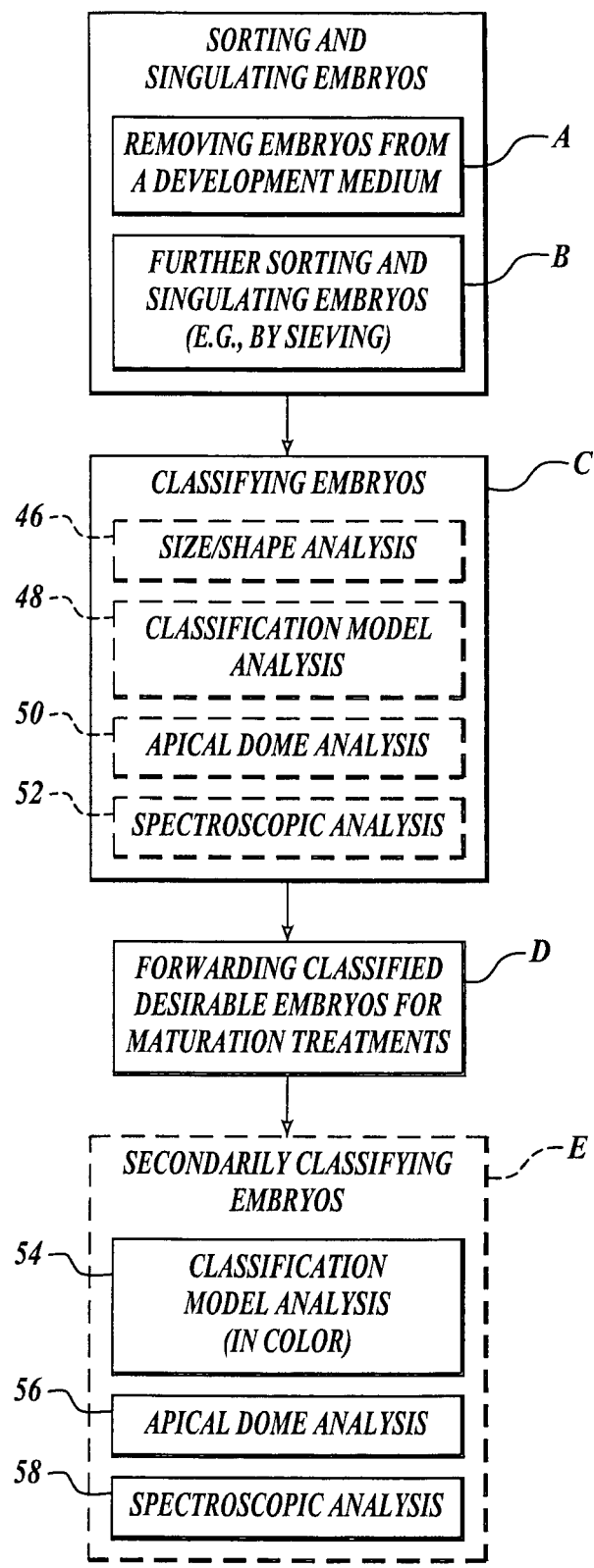
FIG. 2 is a flowchart illustrating an overall flow of a method for automatically harvesting and screening embryos in multiple stages, in accordance with the present invention.

Referring additionally to FIG. 2, a method of the present invention in one embodiment includes generally four steps. First, referring to step "A" in FIGS. 1A and 2, embryos are washed off the development surface (e.g., development pad surface) 16 using pressure-controlled sprays of aqueous liquid (e.g., isotonic nutrient solution) from a suitably arranged nozzle 18. This washing off process separates the culture material including embryos from the development surface 16, but at least some of the embryos remain embedded in or attached to suspensor tissues, residual underdeveloped ESM, and other materials at this point. As illustrated, the development surface 16 may be placed on an inclined surface 20 to facilitate washing off and removal of the culture material including embryos via gravity toward a reservoir 22 (or a hydrocyclone-type separator). The bottom 26 of the reservoir 22 has an elongate opening (slit) extending generally perpendicularly to the direction of a conveyor belt 24 and extending substantially throughout the width of the conveyor belt 24, so that the embryos (embedded in or attached to suspensor tissues or residual ESM) are placed onto the conveyor belt 24 in a generally spread or spatially uniform manner. Alternatively, a flow of liquid-dispersed embryos from the reservoir 22 can be regulated by various other means, such as constriction, flow path length adjustment, etc., to place the embryos on the conveyor belt 24 in a regulated, spatially uniform manner.

Next referring to step "B," the conveyor belt 24 is formed of a porous continuous belt 28 driven by a suitable motor (not shown), which sorts and singulates the embryos by sieving. As used herein, "sorting and singulating" means rudimentarily classifying embryos according to their size/shape and also separating the embryos into discrete units, for example by separating embryos apart and also by removing any undesirable materials from each embryo. For example, sieving by the porous continuous belt 28 achieves both sorting and singulation by causing any undersized material, such as undersized embryos and debris, to drop through its holes.

Specifically, while on the porous continuous belt 28, the embryos perhaps still embedded in suspensor tissues and residual ESM may be further sprayed with aqueous liquid from a second nozzle 30 to cause the embryos (and other adhering materials) to be further dispersed in the aqueous liquid. The liquid spray causes adhering suspensor tissues and residual ESM to be detached from the embryos and washed away and dropped through the porous belt 28. Any undersized or incompletely formed embryos will also be dropped through the porous belt 28. In one embodiment, the conveyor belt 24 may be of a vibrating type, as well known in the conveyor belt technology field, to further facilitate the sorting and singulation process. Any material dropped through the porous belt 28 may be collected in a waste receptacle 32 placed underneath the porous belt 28. Optionally, a second coarser porous belt (not shown) may be provided in series with the first conveyor belt 24 having the first porous belt 28, perhaps prior to the first porous belt 28, to carry away any oversized embryos and other oversized pieces of material. Thus, only those mostly singulated embryos of generally desired size and/or shape, which are more or less free of suspensor tissue and other fine plant material, remain on the first porous belt 28. By adjusting the mesh (hole) size/shape of the porous belt 28 (and of any other additional porous belts), only those embryos within a desirable size/shape range can be selected. It should be noted that, alternatively to the one or more porous conveyor belts described above, one or more sieves of wire or other mesh, for example, vibrating inclined sieves, may be used, although the use of porous conveyor belt(s) is preferred because they sieve and transport (to the next stage) embryos at the same time.

As described above, during steps "A" and "B", the heterogeneous milieu (containing, e.g., acceptable quality embryos, unacceptable embryos, suspensor tissues, residual ESM, and other plant material) is dispersed in aqueous liquid and subjected to separation of components by physical forces (e.g., by sieving) that act differently on the components based on their physical properties (mass, size, shape, specific gravity, drag coefficient, wettability, etc.). As a result, fine plant material and embryo-adhering suspensor tissues are removed, with reduction in amount of any other undesirable components, to produce a population comprising mostly singulated embryos substantially free of suspensor tissues.

After the spray-assisted sieving process, referring to step "C," at the end of the first conveyor belt 24, the sorted and singulated embryos are dropped by gravity onto another conveyor belt, or a classification conveyor belt 34. The classification conveyor belt 34 is arranged generally perpendicularly to the first conveyor belt 24 so that the dropping embryos will generally form a single file 36 along the length of the selection conveyor belt 34 suitable for subsequent imaging. In case the embryos tend to stick to the first conveyor belt 24 and cannot be easily dropped, the separation of the embryos from the first conveyor belt 24 may be assisted by various means. For example, the embryo removal may be assisted by an air/liquid jet (e.g., a gentle squirt of nutrient solution or puff of air-not shown) suitably arranged beneath the porous belt 28 near the end 35 of the first conveyor belt 24, or a fine vibrating wire placed perpendicularly to and just above the first conveyor belt 24 near the end 35, so as to break the surface tension and knock the embryos off the first conveyor belt 24. Alternatively, a dryer (not shown) may be arranged adjacent to the first conveyor belt 24 to dry off the embryos as they move down the first conveyor belt 24.

For the purpose of subsequent imaging, the embryos are sufficiently spaced apart from each other on the classification conveyor belt 34. To achieve sufficient spacing between the embryos in a single file 36, the initial rate of washing off the embryos from the development surface 16 may be adjusted. Also, the configuration of the reservoir 22 (or a hydrocyclone-type separator) may be adjusted, as discussed above, to achieve controlled dispensing of the embryos onto the first conveyor belt 24 and hence controlled dropping of the embryos from the first conveyor belt 24 onto the classification conveyor belt 34. While the reservoir 22 is illustrated to be positioned upstream of the sprayed sieving process in FIG. 1A, it should be understood that the reservoir 22 may be located downstream from the sprayed sieving process, near the end 35 of the first conveyor belt 24, so as to receive and controllably drop the embryos from the first conveyor belt 24 onto the classification conveyor belt 34. As yet another example, an electronic embryo position mapper (not shown) controlled by a computer 40 may be positioned near the end 35 of the first conveyor belt 24 downstream of the sprayed sieving process. The embryo position mapper consists of a suitable optical sensor and detector combination to determine the position of each embryo as it is carried on the first conveyor belt 24. The computer 40, based on the positional information received from the embryo position mapper, continuously adjusts the belt speed of the first conveyor belt 24 and/or the classification conveyor belt 34 so as to achieve a uniform dropping rate of the embryos from the first conveyor belt 24 onto the classification conveyor belt 34. Any of the methods hereinabove described may be combined together. For example, the embryo position mapper positioned near the end 35 of the first conveyor belt 24 may be used to control the initial washing off rate of the embryos from the development surface 16. Also, any other methods for achieving sufficient spacing between the embryos, as they are placed onto the first conveyor belt 24, as will be apparent to one skilled in the art, may be used.

Figure 3A:
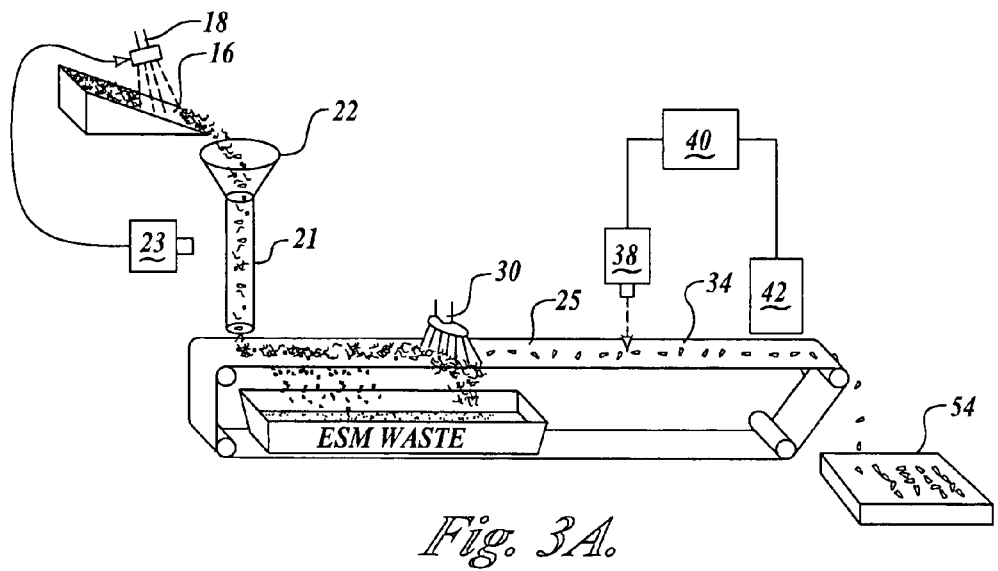
FIGS. 3A and 3B illustrate alternative methods of automatically sorting and singulating embryos, according to the present invention.

In one alternative embodiment, the single file configuration preferred for imaging purposes may be obtained by utilizing the flow of liquid-dispersed embryos along a pipe. Specifically, referring to FIG. 3A, embryos are washed off the development surface 16 using aqueous liquid from a suitably arranged nozzle 18 and placed into a reservoir 22, as with the embodiment illustrated in FIG. 1A. The reservoir communicates with a pipe 21 having a properly chosen diameter, through which the liquid dispersed embryos still entangled with other tissues, ESM, and plant debris, flow, preferably at a predefined controllable velocity, and exit onto the porous conveyor belt 25. In one embodiment, the pipe 21 is clear so that an optical scanner 23 arranged along the clear pipe 21 can observe the flow therethrough to provide feedback to the initial rate of washing off the embryos from the development medium to ensure a desired level of spacing between materials (e.g., embryos) passing through the pipe 21. As before, the conveyor belt 25 is porous, at least in its upstream portion, so that any undersized embryos and other fine materials (suspensor tissues, residual ESM, etc.) fall through the belt 25, as further facilitated by an aqueous liquid spray from the nozzle 30. As illustrated, because the culture stream dispensed from the pipe 21 is generally lined up on the porous conveyor belt 25, the embryos remaining on the belt 25 after the sprayed sieving process are already in a single file configuration 34. Thus, the embryos may continue directly for further classification on the same conveyor belt 25, for example, for image acquisition by a camera 38 and subsequent selective removal of undesirable embryos by an ejector 42, both controlled by the computer 40. The embryos eventually drop from the end of the conveyor belt 25 onto a receiving tray 54, as will be more fully described below.

Figure 3B:
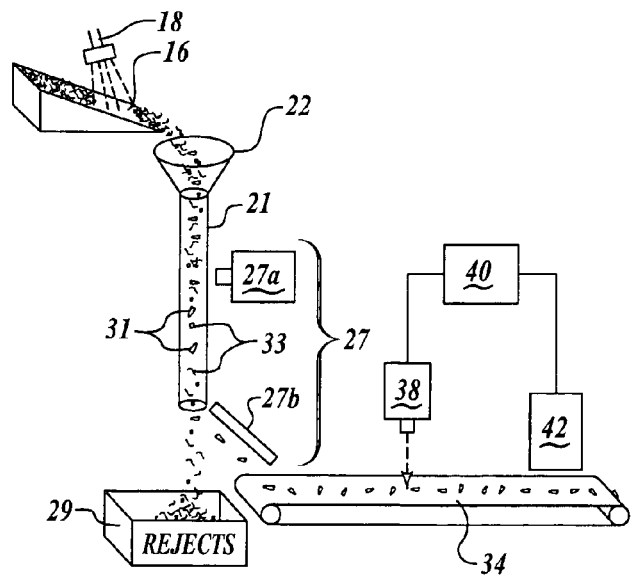

As a further alternative method of achieving the single file configuration, referring to FIG. 3B, a flow cytometer may be used to sort and singulate embryos. In this embodiment, the embryos are washed off the development surface 16 using aqueous liquid from a suitably arranged nozzle 18 and placed into a reservoir 22, as with the previous embodiments, and thereafter travel through a clear pipe 21. A flow cytometer (or cell separator) 27, which is well known in the art, is arranged along the clear pipe 21 to observe and separate the desirable embryos from other materials such as undersized/oversized embryos, suspensor tissues, and residual ESM. Briefly, the flow cytometer differentiates different cells transported in liquid based on the cell properties as observed by optical sensors 27a, and further electrostatically sorts (separates) the cells using deflectors 27b based on ink jet technology, i.e., by deflecting selectively charged liquid droplets containing the targeted cells. In the illustrated embodiment, the flow cytometer 27 is used to sort and separate (branch off) embryos 31 that meet the predefined size/shape criteria onto the classification conveyor belt 34, while other materials 33, such as undersized or oversized embryos and suspensor tissues and residual ESM, drop into a rejects receptacle 29. Therefore, the flow cytometer 27 not only sorts and singulates the embryos, but also places them in a generally single file on the classification conveyor belt 34.

Referring back to FIGS. 1A and 2, in step "C", the sorted and singulated embryos preferably placed in a single file and spaced sufficiently far apart from each other on the classification conveyor belt 34 are classified according to their desirability. For example, each of the embryos may be imaged by a camera 38 placed adjacent to (e.g., above) the classification conveyor belt 34. The image of each embryo is transmitted to the computer 40 to be analyzed and classified according to one or more high-speed algorithms.

In one embodiment, each image (monochromatic or in color) of an embryo is analyzed in two steps. First, referring to FIG. 2, block 46, a suitable algorithm is used to identify those embryos that do not meet basic size and shape criteria to be incorporated into manufactured seeds. Second, referring to block 48, a pre-developed classification model, such as those disclosed in PCT Application Serial No. PCT/US99/12128 (WO 99/63057) discussed above, is applied to the remaining embryos (i.e., the embryos that have met the first size/shape criteria) to identify those embryos having a lower probability of germinating (lacking in germination vigor). Briefly, a suitable classification model can be developed based on a sample population of embryos for which images and actual germination data have been obtained. In a preferred example, a pre-developed classification model to classify embryos according to their putative germination vigor is applied to the same image used in the first size/shape classification step, so that a single image can be used in both of the first and second classification steps. Referring additionally to FIG. 1A, the programs (algorithms) that effect the actual classification and other evaluation of the embryos based on the images produced by the camera 38, e.g.; pre-developed classification models, are stored in the computer 40.

Those embryos rejected either by the first classification step as not meeting the size/shape criteria (block 46) or by the second classification step as not likely to germinate (block 48) may thereafter be ejected from the classification conveyor belt 34, for example, by a precisely timed air/liquid jet 42 controlled by the computer 40 into a waste receptacle 44. The precise timing of the jet activation can be computer controlled because the position of each undesirable embryo is precisely known based on the firing time of the camera 38 that has imaged each embryo and the known speed of the classification conveyor belt 34. The use of an image-actuated precision jet to remove undesirable materials from a conveyor belt is well known in the food industry, for example to sort foods based on their visual characteristics. After undesirable embryos have been removed, only those embryos that have passed both the first and second classification steps remain on the classification conveyor belt 34. Alternatively, the ejector 42 may be configured to remove desirable embryos from the classification conveyor belt 34 onto another location, such as another conveyor belt or a harvest chamber, for further maturation treatments, as will be apparent to one skilled in the art.

The embryo classification step "C" may include further steps or stages of data acquisition and classification/screening operations. For example, after the two-step camera image analysis (blocks 46 and 48 in FIG. 2) is carried out as described above, the embryos may undergo a further imaging analysis (e.g., block 50) or a spectroscopic analysis using IR, NIR, or Raman spectroscopy (block 52), as will be more fully described below, before undesirable embryos are removed from the selection conveyor belt 34. Alternatively, after the two-step camera image analysis described above is completed and any undesirable embryos are ejected, the remaining desirable embryos may be placed in a tray and dried for storage purposes (step "D"), and thereafter (at a later time) undergo further stages of data acquisition and classification, or the "secondary" classification step "E", as will be more fully described below. In other words, in accordance with the present invention, the embryos may undergo any number of classification stages, and further, not all of the classification stages need to occur at the same time.

The camera 38 may be of any suitable type as will be apparent to one skilled in the art, either monochromatic or color, though preferably a digital camera containing a charge-coupled device (CCD) linked to a digital storage device is used so as to permit subsequent digital processing of the acquired image. Further, the camera 38 may be a single-view camera (e.g., taking only the top view of each embryo carried on the classification conveyor belt 34) or a multiple-view camera (e.g., taking the top view, side view, and end view of each embryo). To acquire multiple views of an embryo, one camera may be moved into multiple positions, or multiple cameras may be used. However, preferably, a method and system for simultaneously imaging multiple views of an embryo using a single camera and suitably arranged reflective surfaces (e.g., prisms) may be used so as to shorten the time and operation required to obtain multiple views. Such a method and system for simultaneously imaging multiple views of an embryo are disclosed in a copending U.S. patent application, filed concurrently herewith, titled "Method and System for Simultaneously Imaging Multiple Views of a Plant Embryo", which is explicitly incorporated herein by reference. A classification model algorithm may then be applied to each of the multiple views of an embryo to classify the embryo according to its putative germination vigor.

Additionally or alternatively, during the embryo classification step "C", an apical dome located at the cotyledon end of a plant embryo may be three dimensionally imaged and analyzed to determine the embryo's germinant vigor (i.e., potential for rapid epicotyl development after germination). (See FIG. 2, block 50.) Because the apical dome is where most plant cells that produce the plant body are formed, it has been determined that the dome's morphological features (size, shape, etc.) are reliable indicators of the embryo's tendency for rapid growth after germination. In other words, the three-dimensional information of the apical dome of an embryo can be used as an input to a classification model algorithm to further classify the embryos according to their desirability. Some methods of three-dimensionally imaging an apical dome of a plant embryo can be found in a copending U.S. patent application, filed concurrently herewith, titled Method and System for Three-Dimensionally Imaging an Apical Dome of a Plant Embryo, which is explicitly incorporated herein by reference.

Further additionally or alternatively, during the embryo classification step "C", an embryo may be analyzed using a spectroscopic analysis method, such as IR spectroscopy, NIR spectroscopy, or Raman spectroscopy. (See FIG. 2, block 52). The classification models disclosed in PCT Application Ser. No. PCT/US99/12128 (WO 99/63057) discussed above, may be applied to any absorption, transmittance, or reflectance spectra of embryos, to further qualitatively classify the embryos according to their chemical composition. Briefly, a spectroscopic analysis permits identification of chemistry of each embryo and thus identification of targeted chemical(s) or analytes in an embryo. Embryos that are biochemically mature and likely to germinate are known to include certain levels of targeted chemicals or analytes, such as sugar alcohols. Thus, spectroscopic analysis of embryos is a reliable method of qualitatively identifying biochemically mature embryos. Some methods of spectroscopically analyzing and classifying embryos using NIR spectroscopy are disclosed in PCT Application Serial No. PCT/US99/12128 (WO 99/63057) discussed above. Further, a method of assessing embryo quality using Raman spectroscopy is disclosed in a copending U.S. patent application, filed concurrently herewith, titled "Method for Classifying Plant Embryos Using Raman Spectroscopy" which is explicitly incorporated herein by reference. As used herein, spectroscopic analysis encompasses the analysis of an image taken in one or more specific spectral bands, commonly known as multi-spectral imaging (or chemical imaging, chemical mapping).

It should be noted that other imaging or spectroscopic technologies to determine the biochemical composition or morphological structure of an embryo may be used additionally or alternatively to any of the classification methods described above. As new imaging or spectroscopic technologies emerge or mature, these technologies can be readily incorporated into the present method of automated harvesting and multi-stage screening of plant embryos. For example, Teraherz rays (T-rays) may be used to spectroscopically image a plant embryo to discern its chemical and physical compositions. As a further example, fluorescent labeling technology, such as the quantum dots technology developed by Quantum Dot Corporation of Hayward, Calif., may be used to detect specific compounds and also to track biological events within a plant embryo. Still further, cosmic rays may be utilized to measure the density of an embryo. As will be apparent to one skilled in the art based on these examples, any other technologies that could determine the biochemical or morphological (structural) properties of a plant embryo, based on the use of a broad spectrum of electromagnetic radiation, may be used in accordance with the present invention.

It is noted that the method described hereinabove screens or classifies embryos in multiple stages, first by sieving based on rudimentary size/shape criteria (step "B") then by increasingly sophisticated and hence generally time-consuming means during step "C", such as an image-based size/shape analysis (block 46), image-based classification model analysis (block 48), image-based apical dome analysis (block 50), and spectra-based chemical analysis (block 52). It should be understood that more classification methods may be added as further additional screening criteria are developed. For example, a method of determining the disease resistance of an embryo may be developed using some sensor. Then, a classification stage to classify embryos based on the disease-resistance criteria may be added to further refine the overall classification process. As more screening criteria are developed and their corresponding classification methods incorporated into the present method, the method will be able to identify those embryos that are highly likely to grow into plants that are strong, healthy, and have various other desirable characteristics.

It is contemplated that only those embryos that have passed the previous classification stage will be forwarded to the subsequent screening stage so that a lesser number of embryos need to be evaluated by a later screening stage of perhaps increasing sophistication and complexity, since complex screening stages tend to be more time consuming. However, in some situations two or more screening stages may be carried out in parallel, substantially simultaneously. For example, when multiple views (e.g., the top view, the side view, and the end view) of an embryo are taken and analyzed according to a classification model (block 48), one of the views (e.g., the cotyledon end view containing three-dimensional information of an apical dome) may be simultaneously analyzed in depth to ascertain the morphological features of the embryo's apical dome (block 50).

Still referring to FIGS. 1A and 2, in step "D", at the end of the classification conveyor belt 34, those desirable embryos remaining on the conveyor belt 34 are dropped by gravity (perhaps assisted by an air/liquid jet-not shown) onto a tray (or pad, or any suitable surface) 54 mounted on a two-dimensional drive system (or motorized platform) 56, which is also controlled by the computer 40. The drive system 56 two-dimensionally (or perhaps three-dimensionally) adjusts the position of the tray 54 relative to the end of the classification conveyor belt 34 so as to receive embryos dropping therefrom into an evenly spaced array (e.g., a two-dimensional array). The positioning of the tray 54 relative to the end of the classification conveyor belt 34 is determined based on the precisely known position of each embryo on the classification conveyor belt 34 according to the firing time of the camera 38 and the speed of the conveyor belt 34. Thus, even a somewhat irregularly spaced linear array of desirable embryos on the classification conveyor belt 34 can be transformed into an evenly spaced two-dimensional array on the tray 54. The construction and operation of the drive system 56 should be apparent to one skilled in the art and thus need not be described in detail here. The tray 54, perhaps containing 100 plus embryos arranged in an evenly spaced array, may thereafter be forwarded to receive further maturation treatments. For example, the tray 54 may be forwarded to the Post Development Treatment Room (Drying Room in the illustrated embodiment) 14 to dry the embryos for storage and for subsequent incorporation into manufactured seeds.

Additionally, referring specifically to FIG. 2, in step "E", the embryos placed and dried in the tray 54 may undergo a further, secondary series of classification stages prior to incorporation into manufactured seeds. The embryos may be rehydrated prior to the secondary series of classification stages, or may remain desiccated during one or more of the secondary series of classification stages, depending on each application. As with the previous classification step "C", the secondary classification step "E" may also include one or more classification stages of increasing sophistication and complexity to achieve progressively higher selection accuracy and operational efficiency. Because only a relatively small number of embryos, having passed the previous classification step "C", are remaining at this time, more sophisticated and thus time-consuming classification methods can be carried out, such as the multi-view color imaging analysis using a classification model (block 54), an apical dome analysis (block 56), or a spectroscopic analysis, perhaps also using multiple views (block 58). It is also contemplated that when robotic pick and place systems are used to automatically pick up and insert embryos into manufactured seeds, some digital imaging may be required to ascertain the position of each embryo for that purpose, and therefore this digital imaging can be advantageously combined with image acquisition required for one or more of the classification stages during this secondary classification step "E".

For example, in one embodiment, after being removed from a development medium in step "A", and further being sorted and singulated in step "B", during the embryo classification step "C", the embryos may undergo two classification stages. First, a single-view (e.g., the top view) monochromatic image analysis is carried out to eliminate those embryos that do not meet the basis size/shape criteria (block 46). Second, a classification model is applied to the same single-view monochromatic image to eliminate those embryos that are not likely to germinate (block 48). In step "D", those remaining embryos that have passed both of the two classification stages are placed in a tray and dried. Thereafter, during the secondary classification step "E", the embryos forwarded from step "D" undergo a further series of classification stages that are perhaps more sophisticated and therefore time-consuming. For example, the embryos may be subjected to a multiple-view (e.g., the top view, side view, and end view) color image analysis to eliminate undesirable embryos according to a classification model (block 54), and further to an apical dome analysis (block 56) and/or a spectroscopic analysis (block 58) to still further eliminate undesirable embryos, again according to a suitable classification model.

Figure 1B:
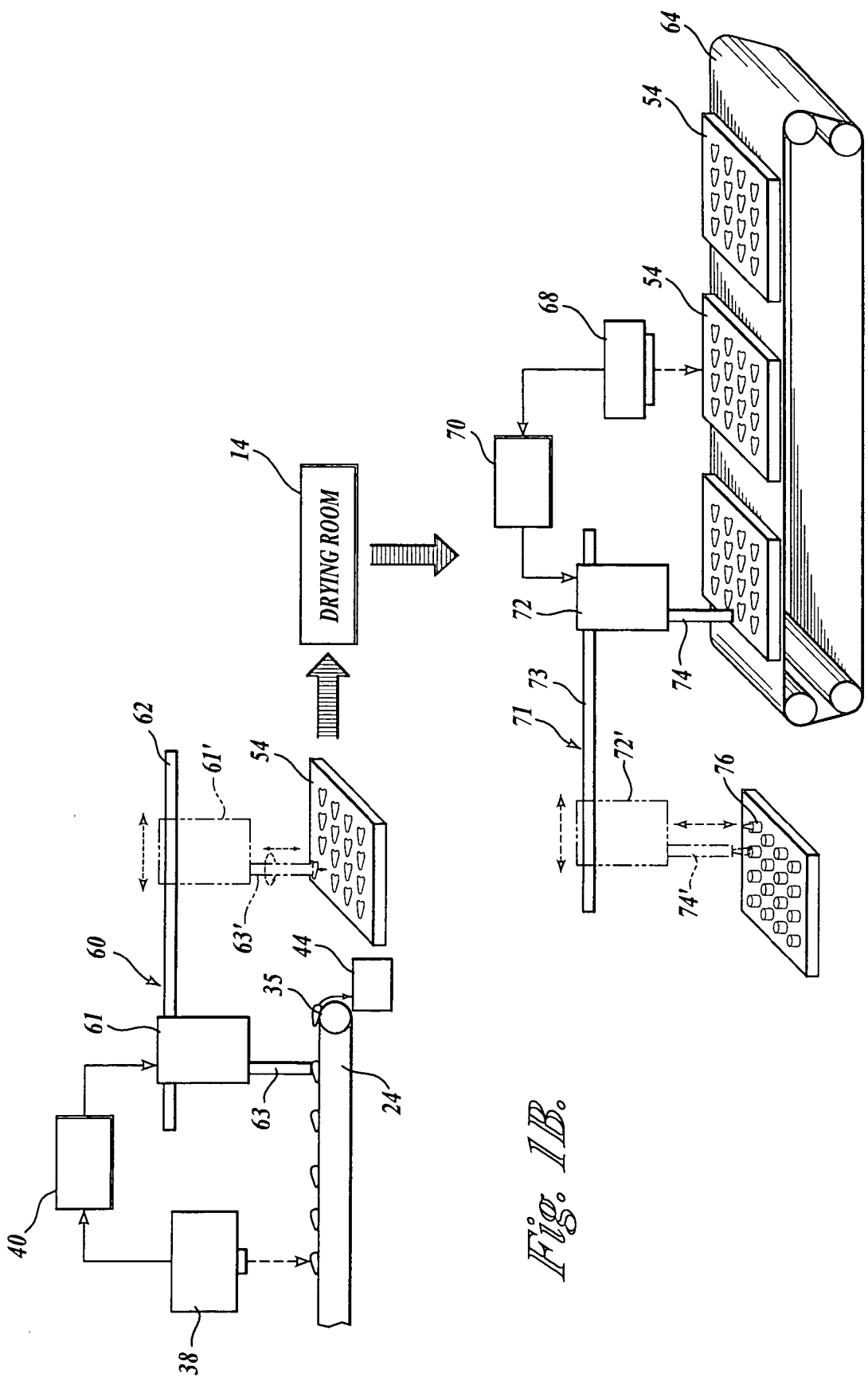
FIG. 1B schematically illustrates an alternative system for automated harvesting and multi-stage screening of plant embryos, in accordance with the present invention.

FIG. 1B illustrates an alternative embodiment of a system for automated harvesting and multi-stage screening of plant embryos. As with the embodiment of FIG. 1A, embryos are washed off a development surface and placed onto the porous conveyor belt 24 and sieved, perhaps as assisted by additional washing with aqueous liquid (corresponding to FIG. 2, steps "A" and "B"). The embryos remaining on the conveyor belt 24 are then imaged by a camera 38. The image of each embryo is transmitted to the computer 40 to be analyzed and classified according to their morphological features (corresponding to FIG. 2, step "C"). For example, a suitable algorithm is used to identify those embryos that meet basic size and shape criteria to be incorporated into manufactured seeds.

Then, a smart mini-robotic transfer system 60 under the control of the computer 40 is used to pick up and place each of those embryos meeting the basic size and shape criteria onto a receiving tray 54 in an evenly spaced array. Briefly, the transfer system 60 includes a housing 61 laterally movable along a rail 62, and a robotic arm 63 extending from the housing 61 and including a vacuum tip end. The robotic arm 63 is longitudinally extendible and also axially rotatable. The details of one example of the mini-robotic transfer system 60 suitable for use in the present embodiment are disclosed in PCT Application Serial No. PCT/US00/40720 (WO 01/13702 A2) incorporated by reference above. In the illustrated embodiment of FIG. 1B, after an embryo is picked up from the conveyor belt 24 by the arm 63, the housing 61 is translated along the rail 62 to a new position 61', at which point the arm 63' is extended downwardly to place the embryo on the tray 54. At this point, the arm 61' may be controllably rotated axially, based on the original orientation of the embryo as imaged by the camera 38 and stored in the computer 40, so that the embryos as placed on the tray 54 are properly oriented, for example, with their cotyledon ends all facing the same direction. In one preferred embodiment, the embryos are precisely placed on the tray 54 in the same orientation and with their cotyledon ends precisely aligned with each other. In the present description, a tray on which embryos are arranged in the same orientation and in a precise array (e.g., with the positions of their cotyledon ends precisely known) is called an "index tray."

Thereafter, the index trays 54 are forwarded to receive maturation treatments, for example to the post development treatment room (drying room in the illustrated embodiment) 14 to dehydrate the embryos (corresponding to FIG. 2, step "D"). Next, the embryos may be rehydrated and undergo a secondary classification process (corresponding to FIG. 2, step "E"). Specifically, the index trays 54 each carrying a properly oriented and evenly spaced array of embryos may be placed on a secondary classification conveyor belt 64, and the embryos may be subjected to additional classification stages as they are transported on the conveyor belt 64. For example, a suitable scanner 68, coupled to a computer 70, is used to further classify the embryos to identify those that are likely to successfully germinate and grow into normal plants. During the secondary classification, the use of the index tray 54 may be advantageous because it permits localized analysis of each embryo on the tray. For example, certain imaging or spectroscopic analysis may be carried out with respect to a localized area of each embryo (e.g., its cotyledon end portion). Because the precise positions of the embryos (e.g., their cotyledon ends) on the index tray 54 are known, such localized analysis is possible.

At the end of the secondary classification conveyor belt 64, another robotic embryo placement system 71 is provided to pick up only those embryos that have been further selected as desirable, and to insert them into manufactured seeds 76. In the illustrated embodiment, the embryo placement system 71 includes a housing 72 translated along a rail 73 and a robotic arm 74 extending from the housing 72. After a desirable embryo is picked up by the arm 74, the housing 72 is translated along the rail 73 to a new position 72', at which point the arm 74' may be lowered to place the embryo into a manufactured seed 76 (or a tubular restraint of the manufactured seed). The details of a suitable embryo placement system is disclosed in PCT Application Serial No. PCT/US00/40720 (WO 01/13702 A2) discussed above. Various other alternative systems for transferring and inserting the embryos into manufactured seeds 76 are possible, as will be apparent to one skilled in the art. For example, the housing 72 and the arm 74 may be two- or three-dimensionally movable. Also, a tray holding the plurality of manufactured seeds 76 may be made one-, two-, or three-dimensionally movable so as to precisely position each of the seeds 76 relative to an embryo carried by the embryo placement system 71.

Notably, because the precise positions of the embryos on the index tray 54 are known, the embryo placement system 71 needs not have the capability to determine or correct the position and/or orientation of each embryo as it is picked up from the tray 54. For example, based on the known position and orientation of each embryo, it is possible for the embryo placement system 71 to precisely position the cotyledon end of each embryo within the manufactured seed 76.

According to the invention, a complete method and system for automatically harvesting somatic embryos are provided, which could replace the current manual operation including the steps of sorting and singulating and further classifying mass-produced embryos according to their putative germination vigor. Classification of the embryos is carried out in multiple stages to efficiently identify those embryos that are suited for incorporation into manufactured seeds. By carefully selecting suitable classification methods to be combined together, one can achieve progressively higher selection accuracy that would match or exceed the level of selectivity currently achievable only by a highly skilled technician. Further, the throughput of the present automated method of multi-stage screening (classification) is calculated to be approximately 5 million embryos per year, which is sufficient to meet the 1.5-2 seconds/embryo rate required for the classification of sorted and singulated embryos for the purpose of mass production of manufactured seeds.

While the preferred embodiments of the invention have been illustrated and described, it will be appreciated that various changes can be made therein without departing from the spirit and scope of the invention.

The embodiments of the invention in which an exclusive property or privilege is claimed are defined as follows:

1. A method of automatically harvesting and screening plant embryos in multiple stages, comprising:
    automatically sorting and singulating plant embryos;
    automatically classifying the sorted and singulated plant embryos using a first classification method; and
    automatically classifying the plant embryos that have passed the first classification method using a second classification method.

2. The method of claim 1, wherein the step of automatic sorting and singulating comprises automatically removing plant embryos from a development medium.

3. The method of claim 2, wherein the automatic removal of plant embryos comprises washing off the plant embryos from the development medium using aqueous liquid.

4. The method of claim 1, wherein the step of sorting and singulating embryos comprises using a flow cytometer.

5. The method of claim 1, wherein the step of sorting and singulating embryos comprises placing the embryos onto a porous material for sieving.

6. The method of claim 5, wherein the embryos placed on the porous material are sprayed with aqueous liquid to remove any suspensor tissues or residual embryonal suspensor masses (ESM) from the embryos.

7. The method of claim 5, wherein the porous material comprises a porous conveyor belt.

8. The method of claim 7, wherein the embryos are placed in a reservoir which dispense the embryos onto the porous conveyor belt, the reservoir being configured to dispense the embryos onto the belt in a regulated manner.

9. The method of claim 8, wherein the reservoir comprises a pipe.

10. The method of claim 7, wherein the plant embryos sorted and singulated after sieving are placed on a classification conveyor belt, along which the first and second automatic classification methods are carried out.

11. The method of claim 10, wherein the sorted and singulated plant embryos are transferred from the porous conveyor belt to the classification conveyor belt by gravity.

12. The method of claim 10, wherein the classification conveyor belt extends generally perpendicularly to the porous conveyor belt.

13. The method of claim 10, wherein the sorted and singulated plant embryos are placed on the classification conveyor belt in a single file along the length of the classification conveyor belt.

14. The method of claim 13, wherein the plant embryos are placed in a single file spaced apart from each other.

15. The method of claim 10, further comprising the step of automatically removing those embryos that have been classified as undesirable by the first or second automatic classification method from the classification conveyor belt.

16. The method of claim 15, wherein the automatic removal of undesirable embryos is carried out by a jet.

17. The method of claim 10, further comprising the step of automatically removing those embryos that have been classified as desirable by the first and second automatic classification methods from the classification conveyor belt.

18. The method of claim 17, wherein the step of automatically removing desirable embryos comprises transferring those desirable embryos onto a receiving surface in a predefined array.

19. The method of claim 18, wherein the receiving surface comprises a tray mounted on a motorized platform configured to adjust the position of the tray relative to the classification conveyor belt so as to receive the embryos dropping by gravity from the classification conveyor belt into a predefined array.

20. The method of claim 19, wherein the dropping of the embryos by gravity from the classification conveyor belt is assisted by a jet.

21. The method of claim 7, wherein the sorted and singulated plant embryos are classified according to the first classification method while on the porous conveyor belt, and the plant embryos that have passed the first classification method are transferred from the porous conveyor belt onto an index tray in a predefined array.

22. The method of claim 21, wherein the second classification method is carried out on the plant embryos that are placed on the index tray.

23. The method of claim 1, wherein the first classification step classifies the embryos based on their shape and size and the second classification step classifies the embryos based on their putative germination vigor according to a predefined classification model.

24. The method of claim 1, wherein the second classification method is more selective and time-consuming than the first classification method.

25. A system for automatically harvesting and screening plant embryos in multiple stages, comprising:
    means for automatically sorting and singulating plant embryos;
    means for automatically classifying the sorted and singulated plant embryos using a first classification method; and
    means for automatically classifying the plant embryos that have passed the first classification method using a second classification method.

* * * * *